United States Patent [19]

de Clercq et al.

[11] 4,382,925

[45] May 10, 1983

[54] E-5-(2-HALOGENOVINYL)-2'-DEOXYCYTIDINES

[75] Inventors: Erik de Clercq; Gabriel A. Verhelst, both of Louvain, Belgium; Albert S. Jones; Richard T. Walker, both of Birmingham, England

[73] Assignees: The University of Birmingham, Birmingham, England; Stichting Rega V.Z.W., Louvain, Belgium

[21] Appl. No.: 193,251

[22] Filed: Oct. 2, 1980

[30] Foreign Application Priority Data

Oct. 3, 1979 [GB] United Kingdom ............... 7934248

[51] Int. Cl.$^3$ ................... A61K 31/70; C07H 19/08
[52] U.S. Cl. ................................ 424/180; 536/23
[58] Field of Search ........................ 424/180; 536/23

[56] References Cited

U.S. PATENT DOCUMENTS

| | | | |
|---|---|---|---|
| 3,354,160 | 11/1967 | Duskinsky et al. | 536/23 |
| 4,000,260 | 12/1976 | Prusoff et al. | 536/23 |
| 4,024,143 | 5/1977 | Schuman et al. | 536/23 |
| 4,267,171 | 5/1981 | Bergstrom et al. | 536/23 |

OTHER PUBLICATIONS

Ruth, J. et al., J. Org. Chem., vol. 43, 2870 (1978).
E. de Clercq et al., J. Carbohydrates, Nucleosides, Nucleotides, 5 (3) 187–224 (1978).
E. de Clercq et al., Proceedings National Academy of Science USA, 76 No. 6, 2947–2951 (1979).
Bergstrom & Ogawa, J.A.C.S., 100, 8106 (1978).
Bergstrom & Ruth, J. Carbohydrates, Nucleosides, Nucleotides, 4 (5) 257–269 (1977).
C. C. Bant, in Synthetic Procedures in Nucleic Acid Chemistry, (R. S. Tipson & W. W. Zorbach, editors) Interscience, vol. 1, 521–522 (1968).
A. S. Jones et al., Tetrahedron Letters, 28, 2459–2460 (1977).
R. C. Bleakley et al., Tetrahedron, 32, 2795–2797 (1976).
E. de Clercq et al., Biochem. Pharmacol. 24, 523–527 (1975).
E. de Clercq et al., Biochem. Pharmacol. 26, 794–797 (1977).
E. de Clercq et al., Molecular Pharmacol. 14, 422–430 (1978).

*Primary Examiner*—Blondel Hazel
*Attorney, Agent, or Firm*—Birch, Stewart, Kolasch & Birch

[57] ABSTRACT

The invention relates to E-5-(2-halogenovinyl)-2'-deoxycytidines, e.g. E-5-(bromovinyl)-2'-deoxycytidine and E-5-(2-iodovinyl)-2'-deoxycytidine. These substances are endowed with specific antiviral activities towards herpes simplex virus and with an extremely low toxicity which makes them useful in antiviral medicines and for treatment of virus diseases in man and animal. They may be synthesized by introduction of an E-5-(2-halogenovinyl) sidechain into 2'-deoxycytidine, or by condensation of a trialkylsilyl derivative of E-5-(2-halogenovinyl)-cytosine with a hydroxyl-protected reactive derivative of 2'-deoxy-D-erythro-pentofuranose.

4 Claims, 1 Drawing Figure

U.S. Patent    May 10, 1983    4,382,925
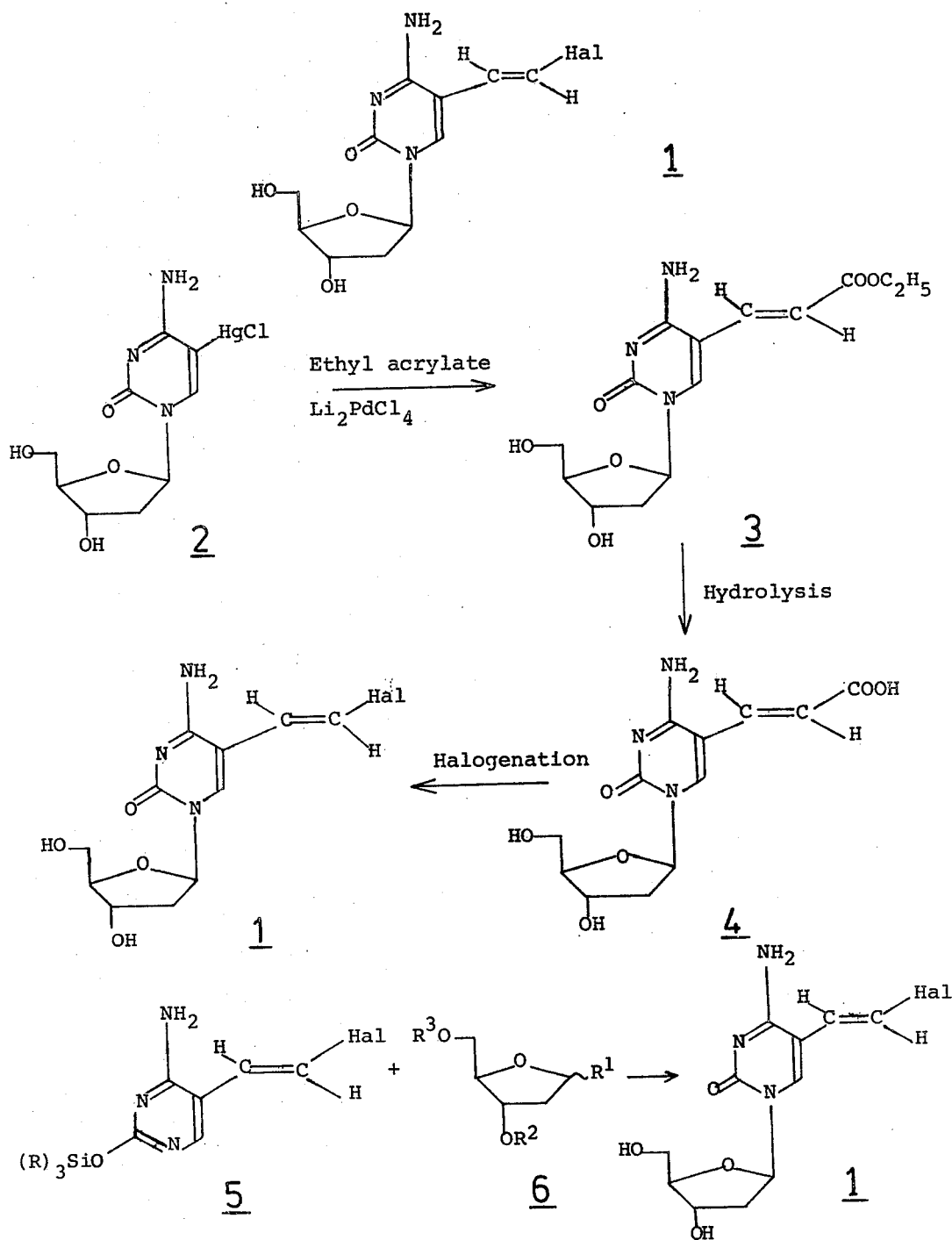

E-5-(2-HALOGENOVINYL)-2'-DEOXYCYTIDINES

This invention relates to E-5-(2-halogenovinyl)-2'-deoxycytidines, for example E-5-(2-bromovinyl)-2'-deoxycytidine and E-5-(2-iodovinyl)-2'-deoxycytidine. Further, it relates to the chemical synthesis of such compounds and to their utilisation in pharmaceutical compositions.

E-5(2-bromovinyl)-2'-deoxycytidine and E-5-(2-iodovinyl)-2'-deoxycytidine, or more systematically E-5(2-bromovinyl)- and E-5-(2-iodovinyl)-1-(2'-deoxy-β-D-erythro-pentofuranosyl)-4-amino-1,2-dihydropyrimidin-2-one, are chemical compounds which may be represented by structural formula 1 of the accompanying formulae drawing wherein Hal is a bromine or iodine atom. It should be noted that in this formula 1 the groups around the vinylic double bond of the halogenovinyl side chain are in the trans- or E-configuration, and that the pyrimidine nucleus is in the beta-position relative to the pentofuranosyl group.

The compounds of formula 1 may be prepared in several ways, e.g. by introduction of an E-5-(2-halovinyl)-, e.g. E-5-(2-iodovinyl)-, side chain into 2'deoxycytidine, or by condensation of a protected reactive 2-deoxy-D-erythro-pentofuranosyl derivative with a trialkylsilyl derivative of E-5-(2-bromovinyl)- or E-5-(2-iodovinyl)-cytosine.

Investigations have indicated that E-5-(2-bromovinyl)-2'-deoxycytidine and E-5-(2-iodovinyl)-2'-deoxycytidine are endowed with an antiviral activity which is very specific towards herpes simplex virus. Moreover, they show an apparent lack of toxicity in cell culture, thus resulting in a high antiviral index against this type of virus and making them useful for the treatment of diseases caused by herpes simplex in man and animal.

The state of the art already comprises a few related deoxycytidine compounds and several related deoxyuridine compounds, all having antiviral activities. A general survey thereof has been given by E. De Clercq et al in J. Carbohydrates-Nucleosides, Nucleotides, 5(3),187–224 (1978) to which attention is directed for further detail. It should be noted, however, that the antiviral activity of most of these compounds is not very specific, since they act equally well against different DNA viruses such as vaccinia and herpes simplex. Moreover, the toxicity of most of these compounds, and especially that of the commonly used standard compound 5-iodo-2'-deoxyuridine, cannot be neglected. Therefore, it is surprising that the compounds E-5-(2-bromovinyl)-2'-deoxycytidine and E-5-(2-iodovinyl)-2'-deoxycytidine have such a specific antiviral activity against one type of virus (herpes simplex) and that their toxicity in cell culture may be nil as stated above.

It should further be noted that specific antiviral activity against herpes simplex virus as well as low toxicity in cell culture have also been reported quite recently for E-5-(2-bromovinyl)-2'-deoxyuridine and E-5-(2-iodovinyl)-2'-deoxyuridine. Compare E. De Clercq et al, in Proceedings National Academy of Science USA, 76, No. 6, 2947-2951 (1979).

When compared with these deoxyuridine counterparts, the compounds of the present invention seem at least equally specific and moreover less toxic and thus suitable for use in pharmaceutical compositions and in the treatment of diseases caused by herpes simplex in man and animal.

Accordingly, the present invention provides E-5-(2-halogenovinyl)-2'-deoxycytidines, e.g. E-5-(2-bromovinyl)-2'-deoxycytidine and E-5-(2-iodovinyl)-2'-deoxycytidine. Further, the invention provides a method of preparing an E-5-(2-halogenovinyl)-2'-deoxycytidine which comprises the introduction of an E-5-(2-halogenovinyl) side chain into 2'-deoxycytidine, or the condensation of a hydroxyl-protected reactive 2-deoxy-D-erythro-pentofuranosyl derivative with a trialkylsilyl derivative of E-5-(2-halogenovinyl)-cytosine. The invention also provides a pharmaceutical composition, which contains at least one E-5-(2-halogenovinyl)-2'-deoxycytidine, preferably E-5-(2-bromovinyl)-2'-deoxycytidine or E-5-(2-iodovinyl)-2'-deoxycytidine, as an active ingredient in a carrier. The invention also provides a method of preparing such a composition comprising combining an E-5-(2-halogenovinyl)-2'-deoxycytidine, preferably E-5-(2-bromovinyl)-2'-deoxycytidine or E-5-(2-iodovinyl)-2'-deoxycytidine, with an excipient.

Chemical synthesis of compounds of the invention will now be described in more detail.

A preferred route of chemical synthesis is shown on the formulae drawing by the diagram including formulae 2,3,4 and 1. This route involves the introduction of an E-5-(2-halogenovinyl)-group into 2'-deoxycytidine by means of a sequence of three steps.

In the first step of this preferred route, 5-chloromercuri-2'-deoxycytidine of formula 2 is reacted with ethyl acrylate in the presence of lithium palladium chloride to form E-5-(2-carbethoxyvinyl)-2'-deoxycytidine of formula 3. The reaction proceeds smoothly at room temperature or slightly above and in a suitable solvent, like dry methanol. Other solvents, e.g. acetonitrile, may be used instead. The reaction mixture may be worked up by treatment with a reducing agent, e.g. $H_2S$ or $NaHB_4$, in order to precipitate reduced palladium and mercury salts. The reaction product is obtainable in good yield and has a trans- or E-configuration, as shown in formula 3.

Instead of ethyl acrylate, the corresponding methyl ester or another lower alkyl acrylate could be used.

This first step is analogous to a reaction step used for preparing 2'-deoxyuridine derivatives, as described by Bergstrom and Ogawa in J.A.C.S., 100, 8106 (1978). The starting material of formula 2 is known in itself and has been described by Bergstrom and Ruth in J. Carbohydrates-Nucleosides, Nucleotides, 4 (5), 257–269 (1977).

In the second step of the preferred route, the E-5-(2-carbethoxyvinyl)derivative of formula 3 is hydrolysed to its corresponding E-5-(2-carboxyvinyl)derivative of formula 4. This hydrolysis may be effected under alkaline or acidic conditions, but acidic conditions are best avoided here in view of the risk of side reactions (e.g. separation of the substituent at the 5-position or separation of the sugar moiety). Hydrolysis under alkaline conditions may be effected with various basic agents, e.g. KOH, NaOH, $K_2CO_3$, $Na_2CO_3$ etc, but the use of KOH is preferred.

In the third step of the preferred route, the E-5-(2-carboxyvinyl)derivative of formula 4 is converted to its corresponding E-5-(2-halogenovinyl)derivative of formula 1. This may be done by halogenation under such conditions that the carboxyl group is removed. Various halogenating agents may be used, e.g. elementary halogen, hydrogen halogenides, hydrogen oxyhalogenides and organic halogenating agents (e.g. N-halogenosuccinimides). Out of this range, hydrogen halogenides and N-halogenosuccinimides are preferred because they have given the best results. Further, a suitable solvent, e.g. water, dimethylformamide, dimethylsulfoxide, etc, may be used as a reaction medium.

The selection of a halogenating agent and a reaction medium will depend upon several factors such as the solubility and stability of the halogenation agent and the solubility of the starting material in the solvent. Thus, N-bromosuccinimide may be used with good results in aqueous media but N-iodosuccinimide as well as elementary bromine and iodine are preferably used in water-free conditions, e.g. in dry dimethylformamide. Further, the starting carboxyvinyl derivative has low solubility in water but this problem can be removed by treatment with aqueous potassium acetate to form the readily soluble potassium salt or by starting directly with an aqueous solution that has been formed during the preceeding step of hydrolysis. The solubility of the starting material in dimethylformamide is somewhat better than in water but nevertheless a combination of potassium acetate and halogenating agent may also be preferable in that case.

As a result of the above three-step synthesis, the desired E-5-(2-halogenovinyl)-2'-deoxycytidine is obtainable in good yield. This end product is a beta-anomer because the desired beta-position of the pyrimidine nucleus relative to the sugar moiety was already present in the starting material. Further, it shows an E-configuration of the halogen atom and pyrimidine nucleus relative to the vinylic double bond, as a result of the selected method. Both facts are advantageous and render the above three-step method preferable.

A second but less preferred route of synthesis has been shown on the formulae drawing by the diagram including formulae 5,6 and 1. This route comprises a condensation reaction between a trialkylsilyl derivative of E-5-(2-halogenovinyl)-cytosine (formula 5) and a hydroxyl-protected reactive 2-deoxy-D-erythro-pentofuranosyl derivative (formula 6) to form the desired end product. In these formulae, R is an alkyl group, preferably methyl; $R^1$ is a readily displaceable group, preferably either methoxy or chloro; $R^2$ and $R^3$ are hydroxyl-protecting groups, preferably p-toluoyl; Hal is e.g. bromine or iodine and ~ denotes and alpha- and/or beta-configuration.

The condensation reaction will proceed smoothly under the influence of a Lewis acid catalyst, such as a molecular sieve, stannic or mercuric chloride or bromide, or trimethylsilyl perfluoralkylsulphonate. Further, a solvent may be present which is inert to the reactants and to the product and which preferably dissolves the reactants and catalyst to a sufficient degree. Suitable solvents are e.g. acetonitrile, benzene, toluene, dichloromethane, 1,2-dichloroethane and carbon tetrachloride. The reaction should be carried out in a dry atmosphere to prevent hydrolysis of the trialkylsilyl derivative of formula 5. The reaction temperature is not critical but will mostly be room temperature or below.

After completion of the reaction and working up of the reaction mixture, the protecting groups may be removed from the resulting product by standard methods, e.g. hydrolysis or alcoholysis.

This second route of chemical synthesis usually produces a mixture of alpha- and beta-anomers which mixture should be separate since only the beta-anomer is desired. Such separation is mostly effected before removal of the hydroxyl protecting groups and may be carried out by fractional crystallisation and/or by chromatography on silica gel. The whole separation step is rather inconvenient however, and therefore, the second route of synthesis is less preferred.

The starting materials of formula 6 have been described earlier and may be prepared from 2-deoxy-D-erythropentofuranose by methylation of the 1-hydroxyl group, incorporation of protecting groups to the hydroxyl groups at 3 and 5, and where required by replacement of the 1-methoxy group by a chlorine atom (compare e.g. C. C. Bath, in Synthetic Procedures in Nucleic Acid Chemistry, by Tipson R. S. and Zorbach W. W., eds, Interscience, Vol. 1, 521–522 (1968)).

The other starting material may be prepared by silylating E-5-(2-halogenovinyl)-cytosine (formula 5) with a silylating agent such as hexamethyldisilazane or trimethylchlorosilane or mixtures thereof (compare A. S. Jones et al, Tetrahedron Letters, 28, 2459–2460 (1977) for a similar reaction). The E-5-(2-halogenovinyl)-cytosine may simply be obtained by brominating or iodinating 5-vinylcytosine followed by the elimination of HBr or HI by the action of heat (compare R. C. Bleakley et al, Tetrahedron, 32, 2795–2797 (1976) for an analogous reaction on 5-vinyluracil). Further, said E-5-(2-halogenovinyl)-cytosine may be obtained from 5-formylcytosine by reaction with malonic acid to form E-5-(2-carboxyvinyl)-cytosine followed by a suitable halogenation in the same way as described above for the first synthetic route.

The first route of chemical synthesis as well as the physical constants of the end products are illustrated further in the following examples, which should not be contrued however, as restricting the invention.

EXAMPLE 1

(a) E-5-(2-carbethoxyvinyl)-2'-deoxycytidine (formula 3)

5-chloromercuri-2'-deoxycytidine (4.62 g, 10 mmol), (formula 2), ethyl acrylate (6 g, 60 mmol) and 0.1M $Li_2Pd Cl_4$ in dry methanol (100 ml) are combined in a 250 ml round-bottom flask and stirred under nitrogen for 24 hrs to give a black suspension. This is filtered and the black precipitate collected. The latter is warmed in methanol (100 ml) and filtered. The combined filtrates are treated with $NaBH_4$ until the precipitation of black material is complete and the solution colourless. After another filtration the solution is concentrated under reduced pressure (to 30 ml) from which the title compound crystallises (1.4 g, 43%). U.V. spectrum: (Ethanol)

$\lambda_{min}$237 nm ($\epsilon$8.230)$\lambda_{max}$268 nm ($\epsilon$17.430)$\lambda_{min}$ 297 nm ($\epsilon$8.250)$\lambda_{max}$ 327 nm ($\epsilon$13.920) at pH 2; $\lambda_{max}$ 221 nm ($\epsilon$21.670) $\lambda_{min}$ 245 nm ($\epsilon$8.560) $\lambda_{max}$ 275 nm ($\epsilon$13.730)$\lambda_{min}$ 297 nm ($\epsilon$8.050)$\lambda_{max}$326 nm ($\epsilon$14.260) at pH 7.

N.M.R. spectrum:

S ($d_6$DMSO); 8.50 (s, 1H, H-6), 7.57 (d, 1H, vinylic H, J=16 Hz) 7.42 (s, 2H, $NH_2$) 6.21 (d, 1H, vinylic H, J=16 Hz) 6.10 (t, 1H, H-1') 5.16 (d, 1H, CH-3') 5.14 (t, 1H, OH-5') 4.20 (m, 1H, H-3') 4.13 (g, 2H, $\underline{CH_2}$—$CH_3$) 3.79 (m, 1H, H-4') 3.62 (m, 2H, H-5') 2.13 (m, 2H, H-2') 1.24 (t, 3H, $CH_2$—$\underline{CH_3}$).

The starting material, 5-chloromercuri-2'-deoxycytidine has been obtained by the method of Bergstrom and Ruth, J. Carbohydrates-Nucleosides, Nucleotides, 4 (5), 257–269 (1977).

(b) E-5-(2-carboxyvinyl)-2'-deoxycytidine (formula 4)

Carbethoxyvinyldeoxycytidine (325 mg, 1mmol) is suspended in 0.5M NaOH solution (40 ml) and stirred at room temperature for 2 hrs. The clear solution is neutralised by addition of Dowex-50H+-form to pH 7 and filtered. This solution is immediately used for the preparation of E-5-(2-bromovinyl)-2'-deoxycytidine.

(c) E-5-(2-bromovinyl)-2'-deoxycytidine (formula 1, Hal=Br)

A solution by hydrolysis of carbethoxyvinyldeoxycytidine (325 mg, 1 mmol) as described above, is treated with N-bromosuccinimide (178 mg, 1 mmol) and stirred at room temperature for 15 hrs. After removal of the solvent the residue is purified on $SiO_2$ (50 g) with $CHCl_3$-MeOH (80:20) as eluant giving the title compound (150 mg, 48%, Rf=0.32). U.V. spectrum: (water)

$\lambda_{max}$244 nm ($\epsilon$16.090)$\lambda_{min}$280 nm ($\epsilon$5.260)$\lambda_{max}$ 302 nm($\epsilon$7.610) at pH 2; $\lambda_{max}$250 nm (68 15.830)$\lambda_{min}$286 nm ($\epsilon$6.390)$\lambda_{max}$ 292 nm ($\epsilon$6.590) at pH 7; $\lambda_{max}$ 249 nm (68 17.360) $\lambda_{min}$283 nm ($\epsilon$7.300)$\lambda_{max}$292 nm ($\epsilon$7.660) at pH 11.

N.M.R. spectrum:

$\delta$(d$_6$DMSO); 8.10 (s, 1H, H-6) 7.21 (br, 2H, NH$_2$) 7.05 (d, 1H, vinylic-H, J=13 Hz) 6.70 (d, 1H, vinylic-H, J=13 Hz) 6.10 (t, 1H, H-1') 5.05 (br, 2H, OH-3' and OH-5') 4.10 (m, 1H, H-3') 3.75 (m, 1H, H-4') 3.60 (m, 2H, H-5') 2.10 (m, 2H, H-2')

EXAMPLE 2

(a) E-5-(2-carbethoxyvinyl)-2'-deoxycytidine is prepared in the same way as described in Example 1(a).

(b) E-5-(2-carboxyvinyl)-2'-deoxycytidine is prepared by hydrolysis along the lines of Example 1(b) with the exception that after neutralisation and filtration, the solvent is removed in vacuo from the solution and the reside is dried over $P_2O_5$.

(c) E-5-(2-iodovinyl)-240 -deoxycytidine (formula 1, Hal=I)

The residue resulting from step 2(b) is suspended in dry DMF (20 ml) and N-iodosuccinimide (225 mg, 1 mmol) is added. The mixture is stirred at room temperature for 4 hrs and worked up as usual to give the title compound (105 mg, 28%). U.V. spectrum: (Ethanol)

$\lambda_{max}$258 nm ($\epsilon$17.282)$\lambda_{sh}$200 nm ($\epsilon$7.504) at pH 7; $\lambda_{max}$ 256 nm ($\epsilon$15.160)$\lambda_{min}$293 nm ($\epsilon$4.700)$\lambda_{max}$315 nm ($\epsilon$6.216) at pH 2.

N.M.R. spectrum:

$\delta$(d$_6$DMSO); 8.06 (s, 1H, H-6) 7.26 (d, 1H, vinylic H, J=14 Hz) 7.20 (br, 2H, NH$_2$) 6.64 (d, 1H, vinylic H, J=14 Hz) 6.08 (t, 1H, H-1') 5.11 (d, 1H, OH-3') 5.03 (t, 1H, OH-5') 4.20 (m, 1H, H-3') 3.76 (m, 1H, H-4') 3.58 (m, 2H, H-5') 2.08 (m, 2H, H-2').

BIOLOGICAL TESTS

Reference will now be made to a series of biological tests to show the specific antiviral activity, low toxicity and high antiviral index of compounds of the invention.

In these tests, the effect of E-5-(2-halogenovinyl)-2'-deoxycytosine and related compounds on the growth and yield of viruses in cell cultures was measured.

The compounds tested were: E-5-(2-bromovinyl)-2'-deoxycytidine and E-5-(2-iodovinyl)-2'-deoxycytidine (prepared in accordance with the foregoing examples); E-5-(2-bromovinyl)-2'-deoxyuridine and E-5-(2-iodovinyl)-2'-deoxyuridine; and 5-iodo-2'-deoxyuridine (provided by Ludeco, Brussels). All compounds were $\beta$-anomers.

The compounds were tested on vaccinia virus and three strains of herpes simplex-1 virus (strain KOS, strain McIntyre and strain F). These viruses were grown in primary rabbit kidney (PRK) and human skin fibroblast (HSF) cell cultures.

The technique for measuring virus growth in cell cultures has been described by De Clercq et al., Biochem. Pharmacol. 24, 523–527, (1975).

TEST 1

In this test, the inhibitory activity of E-5-(2-halogenovinyl)-2'-deoxycytidines and related compounds to vaccinia and herpes simplex-1 viruses in PRK and HSF cell cultures was measured. The cells were grown to confluency in plastics microplates (PRK, HSF). When confluent, the cells were inoculated with 100 CCID$_{50}$ of either vaccinia or herpes simplex-1 virus. One CCID$_{50}$ or "cell culture infecting dose-50", is the virus dose required to infect 50% of the cell cultures. One hour after virus inoculation, the compounds were added at varying concentrations (ranging from 0.001 $\mu$g/ml to 100 $\mu$g/ml). For each virus-cell system, the ID$_{50}$ was determined. ID$_{50}$ or "inhibitory dose-50" is the concentration of compound required to suppress the cytopathic effect on the virus by 50%.

TABLE 1

Antiviral activity of E-5-(2-halogenovinyl-2'-deoxycytidines and related compounds in PRK and HSF cell cultures.

| Compound | ID$_{50}$ ($\mu$g/ml) | | | | | |
|---|---|---|---|---|---|---|
| | Vaccinia (PRK) | Vaccinia (HSF) | Herpes simplex-1 strain KOS (PRK) | Herpes simplex-1 strain KOS (HSF) | Herpes simplex-1 strain McIntyre (PRK) | Herpes simplex-1 strain F (PRK) |
| E-5-(2-bromovinyl)-2'-deoxycytidine | 10 | 2 | 0.07 | 0.07 | 0.07 | 0.1 |
| E-5-(2-bromovinyl)-2'-deoxyuridine | 7 | 0.7 | 0.007 | 0.01 | 0.01 | 0.01 |
| E-5-(2-iodovinyl)-2'-deoxycytidine | 10 | 7 | 0.1 | 0.07 | 0.07 | 0.2 |
| E-5-(2-iodovinyl)-2'-deoxyuridine | 10 | 1 | 0.01 | 0.02 | 0.01 | 0.01 |
| 5-iodo-2'-deoxyuridine | 0.02 | 0.2 | 0.1 | 0.2 | 0.15 | 0.2 |

This cytopathic effect (CPE) was recorded as soon as it reached completion in the untreated virus-infected cell cultures (generally, 3 days after the cells have been inoculated with the virus). The results are given in Table 1, where the data represent average values for three separate experiments.

From Table 1, it can be seen that the E-5-(2-halogenovinyl)-2'-deoxycytidines, although somewhat less active than their deoxyuridine counterparts, were equally active or slightly more active against herpes simplex-1 than the standard compound 5-iodo-2'-deoxyuridine. Further, it can be seen that contrary to the standard compound, the E-5-(2-halogenovinyl)-2'-deoxycytidines have an antiviral activity which is very specific against herpes simplex-1 virus. This specificity is about the same as that of their deoxyuridine counterparts.

TEST 2

Further, the inhibitory effect of E-5-(2-halogenovinyl)-2'-deoxycytidines and a related compound on herpes simplex-1 (strain KOS) virus multiplication in PRK cell cultures was measured.

Confluent PRK cell monolayers in plastics Petri dishes (diameter: 55 mm) were inoculated with herpes simplex-1 (4.5 $\log_{10}$ PFU/0.5 ml/Petri dish) for 1 hour at 37° C. and, immediately thereafter, exposed to 0.1 μg/ml of either of the compounds to be tested. The cell cultures were then incubated for varying times (1,2 or 3 days) at 37° C. At the end of the incubation period the cells were frozen at −70°, and the cell homogenates were assayed for virus content by plaque formation in VERO cell cultures (VERO=a continuous cell line of green monkey cells). The results are presented in Table 2 as the differences in virus yield between the treated virus-infected cell cultures and the untreated virus-infected cell cultures. PFU means plaque formation units.

TABLE 2

Inhibitory effect of E-5-(2-halogenovinyl)-2'-deoxycytidines on herpes simplex-1 (strain KOS) virus multiplication in PRK cell cultures.

| Compound | Dose (μl/ml) | Reduction in virus yield ($\log_{10}$ PFU/ml), as compared to control (untreated virus-infected) cell cultures Days after infection | | |
|---|---|---|---|---|
| | | 1 | 2 | 3 |
| E-5-(2-bromovinyl)-2'-deoxycytidine | 10 | 3.8 | 2.9 | 2.2 |
| E-5-(2-iodovinyl)-2'-deoxycytidine | 10 | 4.3 | 2.8 | 2.0 |
| 5-iodo-2'-deoxyuridine | 10 | 4.0 | 2.6 | 1.9 |

It can be seen from Table 2 that the reduction in virus yield brought about by the E-5-(2-halogenovinyl)-2'-deoxycytidines is comparable to that of the standard compound 5-iodo-2'-deoxyuridine.

TEST 3

The antimetabolic activity of E-5-(2-halogenovinyl)-2'-deoxycytidines and related compounds in PRK cell cultures was measured.

To this end, the incorporation of certain radiolabelled DNA precursors into DNA of the cells, and the effect of 5-(2-halogenovinyl)-2'-deoxycytidines and related compounds thereon, was tested. The technique has been described by De Clercq et al in Biochemical Pharmacology, 26, 794–797 (1977) and by De Clercq et al in Molecular Pharmacology, 14, 422–430, (1978).

The DNA precursors as used were (methyl-$^3$H), (2'-deoxythymidine ) (TdR), and (2-$^{14}$C) (2'-deoxyuridine) (UdR).

The cells were exposed to 0.12 μCi:0.01 nmol (methyl-$^3$H)TdR (per $10^5$ cells) or 14 μCi/250 nmol (2-$^{14}$C) UdR (per $10^5$ cells) for 16 hours in the presence of varying concentrations of the compounds (ranging from 1 to 200 μg/ml). Incorporation of the radiolabelled precursor was then measured as described and the ID$_{50}$ was determined. ID$_{50}$ corresponds to the inhibitory dose-50, that is the concentration of compound required to inhibit incorporation of either (methyl-$^3$H)TdR or (2-$^{14}$C)UdR by 50%. The results are given in Table 3.

TABLE 3

Antimetabolic activity of E-5-(2-halogenovinyl)-2'-deoxycytidines and related compounds in PRK cell cultures.

| | ID$_{50}$ (μg/ml) | |
|---|---|---|
| Compounds | (Methyl-$^3$H)TdR incorporation into cell DNA | (2-$^{14}$C)UdR incorporation into cell DNA |
| E-5-(2-bromovinyl)-2'-deoxycytidine | >>200 | >>200 |
| E-5-(2-bromovinyl)-2'-deoxyuridine | 100 (70) | 100 (70) |
| E-5-(2-iodovinyl)-2'-deoxycytidine | >>200 | >>200 |
| E-5-(2-iodovinyl)-2'-deoxyuridine | 80 (70) | 150 (70) |
| 5-iodo-2'-deoxyuridine | (2.5) | (1.2) |

N.B. The data in parentheses have been obtained in separate experiments as reported by De Clercq et al. in Proceedings of the National Academy of Sciences (USA), 76, 2947–2951 (1979).

It can be seen from Table 3 that neither of the E-5-(2-halogenovinyl)-2'-deoxycytidines caused any inhibition of the incorporation of (methyl-$^3$H)TdR or (2-$^{14}$C)UdR into cellular DNA, even at 200 μg/ml, the highest concentration tested.

TEST 4

Finally, the antiviral index of E-5-(2-halogenovinyl)-2'-deoxycytidines and related compounds in PRK cell cultures was determined as a result of the measurements made in the foregoing tests.

The antiviral index was determined as the ratio of ID$_{50}$ for (2-$^{14}$C)UdR incorporation into cell DNA to ID$_{50}$ for herpes simplex-1 (strain KOS) virus replication (compare Tables 1 and 3). The results are given in Table 4.

TABLE 4

Antiviral index of E-5-(2-halogenovinyl)-2'-deoxycytidines and related compounds in PRK cell cultures.

| Compound | Antiviral index |
|---|---|
| E-5-(2-bromovinyl)-2'-deoxycytidine | >>3000 |
| E-5-(2-bromovinyl)-2'-deoxyuridine | 14300 (10000) |
| E-5-(2-iodovinyl)-2'-deoxycytidine | >>2000 |
| E-5-(2-iodovinyl)-2'-deoxyuridine | 15000 (7000) |
| 5-iodo-2'-deoxyuridine | (12) |

N.B. Compare footnote to Table 3 for numbers in parentheses.

From Table 4, it can be seen that the antiviral index for the invented E-5-(2-halogenovinyl)-2'-deoxycytidines amounts to (much) more than 2000–3000. As these compounds did not show toxicity at the highest concentration tested (200 ug/ml), their exact antiviral index could not be determined accurately.

It will be noted from the foregoing that E-5-(2-bromovinyl)-2'-deoxycytidine and E-5-(2-iodovinyl)-2'-deoxycytidine are endowed with an excellent and highly specific antiviral activity against herpes simplex virus and that their toxicity in cell culture is apparently nil. Compared with the corresponding E-5-(2-halogenovinyl)-2'-deoxyuridines, they may have a higher specificity towards herpes simplex virus and a lower toxicity to living cells in cell cultures. Although the absolute value of their antiviral activity may be somewhat lower than that of the 2'-deoxyuridine analogues, their apparent lack of toxicity in cell culture suggests that the compounds may eventually achieve therapeutic indices that are as high or even higher than those attained by the 2'-deoxyuridine analogues. Thus, they may be used with advantages for preparing pharmaceutical compositions and for treatment of diseases caused by herpes simplex virus in man and animal.

Pharmaceutical compositions comprising E-5-(2-bromovinyl-2'-deoxycytidine or E-5-(2-iodovinyl)-2'-deoxycytidine as an active ingredient may have the form of powders, suspensions, solutions, emulsions as well as ointments and pastes, and may be used for parenteral (intradermal, intramuscular, intrathecal, . . . ) injections, oral, rectal, intravaginal and intranasal administrations or topical application (e.g. to lesions of skin, mucosa and eye). These compositions may be prepared by combining the active ingredient(s) with pharmacutically acceptable excipients which are normally used for this purpose. These excipients may comprise aqueous or non-aqueous solvents, stabilisers, suspenders, dispersers, wetting agents and the like and will be known to the skilled in the pharmaceutical art. Further, the composition may include any suitable additives like polyethyleneglycols, and, if desired, dyestuffs, perfumes and the like.

The pharmaceutical compositions will normally contain at least 0.1% by weight/volume of the active ingredient. The actual concentration will depend on the disease and on the chosen route of administration. In general, this concentration will be between 0.1% and 100%.

We claim:

1. E-5-(2-halogenovinyl)-2'-deoxycytidines selected, in particular, from the group consisting of E-5-(2-bromovinyl)-2'-deoxycytidine and E-5-(2-iodovinyl)-2'deoxycytidine.

2. A method of preparing an E-5-(2-halogenovinyl)-2'-deoxycytidine which comprises introducing an E-5-(2-halogenovinyl)-group into 2'-deoxycytidine by the steps of reacting 5-chloromercuri-2'-deoxycytidine with an ethyl acrylate in the presence of a lithium palladium chloride catalyst, hydrolyzing the resulting E-5-(2-carbethoxyvinyl)-2'deoxycytidine and halogenating the resulting E-5-(2-carboxyvinyl)-2'-deoxycytidine to form E-5-(2-halogenovinyl)-2'-deoxycytidine.

3. A method of treating herpes simplex infections, which comprises administering a therapeutically effective amount of E-5-(2-halogenovinyl)-2'-deoxycytidine to a patient suffering from herpes simplex infection.

4. An antiviral pharmaceutical composition having special usefulness for treatment of herpes simplex infections, said pharmaceutical composition comprising an effective amount of E-5-(2-halogenovinyl)-2'-deoxycytidine, selected in particular from the group consisting of E-5-(2-bromovinyl)-2'-deoxycytidine and E-5-(2-iodovinyl)-2'-deoxycytidine with a pharmaceutically acceptable excipient.

* * * * *